United States Patent
Tanioka (10) Patent No.: US 10,473,681 B2
(45) Date of Patent: Nov. 12, 2019

(54) MEASURING APPARATUS AND MEASURING METHOD

(71) Applicant: Toshiba Memory Corporation, Tokyo (JP)

(72) Inventor: Chikara Tanioka, Kanagawa (JP)

(73) Assignee: Toshiba Memory Corporation, Tokyo (JP)

(*) Notice: Subject to any disclaimer, the term of this patent is extended or adjusted under 35 U.S.C. 154(b) by 0 days.

(21) Appl. No.: 16/102,825

(22) Filed: Aug. 14, 2018

(65) Prior Publication Data
US 2019/0204352 A1    Jul. 4, 2019

(30) Foreign Application Priority Data

Dec. 28, 2017  (JP) .................................. 2017-254368

(51) Int. Cl.
*G01B 9/021*    (2006.01)
*G01P 5/00*    (2006.01)
(Continued)

(52) U.S. Cl.
CPC ............... *G01P 5/001* (2013.01); *G03H 1/28* (2013.01); *G03H 2001/0033* (2013.01); *G03H 2226/11* (2013.01)

(58) Field of Classification Search
CPC ............... G01B 9/021; G01B 9/02047; G01B 9/02083; G01B 9/02087; G01N 21/453; G03H 1/0005; G03H 2001/0033
(Continued)

(56) References Cited

U.S. PATENT DOCUMENTS 5,548,419 A * 8/1996 Adrian .................... G01P 5/001
                                                              359/10
6,496,262 B1 * 12/2002 Meng ....................... G01P 5/001
                                                              356/339
(Continued)

FOREIGN PATENT DOCUMENTS

JP    2002-131015 A    5/2002
JP      3888829 B2     3/2007
(Continued)

OTHER PUBLICATIONS

Digital holographic particle image velocimetry, Ooms, T.A. ISBN 978-90-9023273-7 (Year: 2008).*
(Continued)

*Primary Examiner* — Shawn Decenzo
*Assistant Examiner* — Jonathon Cook
(74) *Attorney, Agent, or Firm* — Finnegan, Henderson, Farabow, Garrett & Dunner, L.L.P.

(57) ABSTRACT

According to one embodiment, a beam splitter splits light into first light and second light. The second light is used to irradiate a sample containing particles. A first imaging device images a first interference pattern formed by multiplexing third light, which has been generated by irradiating the particles with the second light, and the first light. A second imaging device images a second interference pattern formed by the third light. An arithmetic device compares a composite image with a calculated image. The composite image is created by using a first interference image picked up by the first imaging device and a second interference image picked up by the second imaging device. The calculated image is obtained by combining single particle interference images, each of which is expected to be obtained by the first imaging device in a case where a particle is present alone in the sample.

20 Claims, 7 Drawing Sheets

(51) Int. Cl.
*G03H 1/28* (2006.01)
*G03H 1/00* (2006.01)

(58) Field of Classification Search
USPC .......................................... 356/457
See application file for complete search history.

(56) References Cited

U.S. PATENT DOCUMENTS

| | | | |
|---|---|---|---|
| 6,867,410 B2 | 3/2005 | Sasaki et al. | |
| 2002/0159047 A1* | 10/2002 | Dubois | G01P 5/26 |
| | | | 356/28.5 |
| 2011/0043607 A1* | 2/2011 | Grier | G01N 15/0227 |
| | | | 348/40 |
| 2017/0219998 A1* | 8/2017 | Hong | G03H 1/0866 |
| 2018/0189963 A1* | 7/2018 | Joly | G06T 7/248 |

FOREIGN PATENT DOCUMENTS

| | | |
|---|---|---|
| JP | 2015-78969 A | 4/2015 |
| JP | 2017-161436 A | 9/2017 |

OTHER PUBLICATIONS

Single beam two-views holographic particle image velocimetry. Sheng et al, Applied Optics vol. 42, Issue 2, pp. 235-250 (2003) (Year: 2003).*

* cited by examiner

| PARTICLE STATE | | | | SINGLE PARTICLE INTER-FERENCE IMAGE |
|---|---|---|---|---|
| PARTICLE POSITION | | | COMPLEX AMPLITUDE | |
| x-COORDINATE | y-COORDINATE | z-COORDINATE | | |
| x1 | y1 | zo1 | A1 | |
| x2 | y1 | zo1 | A1 | |
| x3 | y1 | zo1 | A1 | |
| x1 | y2 | zo1 | A1 | |
| x1 | y3 | zo1 | A1 | |
| x1 | y1 | zo2 | A1 | |
| x1 | y1 | zo3 | A1 | |
| ... | ... | ... | ... | ... |

MEASURING APPARATUS AND MEASURING METHOD

CROSS-REFERENCE TO RELATED APPLICATIONS

This application is based upon and claims the benefit of priority from Japanese Patent Application No. 2017-254368, filed on Dec. 28, 2017; the entire contents of which are incorporated herein by reference.

FIELD

An embodiment described herein relates generally to a measuring apparatus and a measuring method.

BACKGROUND

As a conventional method for measuring three dimensional information about particles in liquid, Digital Holographic Particle Image Velocimetry (which will be referred to as "DHPIV") is known.

DETAILED DESCRIPTION

In general, according to one embodiment, a measuring apparatus includes a light source, a beam splitter, a first imaging device, a second imaging device, and an arithmetic device. The beam splitter splits light from the light source into first light and second light. The second light is used to irradiate a sample containing particles treated as measuring objects. The first imaging device images a first interference pattern formed by multiplexing third light, which has been generated by irradiating the particles with the second light, and the first light. The second imaging device images a second interference pattern formed by the third light. The arithmetic device compares a composite image with a calculated image. The composite image is created by using a first interference image picked up by the first imaging device and a second interference image picked up by the second imaging device. The calculated image is obtained by combining single particle interference images, each of which is expected to be obtained by the first imaging device in a case where a particle is present alone in the sample.

An exemplary embodiment of a measuring apparatus and a measuring method will be explained below in detail with reference to the accompanying drawings. The present invention is not limited to the following embodiment.

Figure 1:
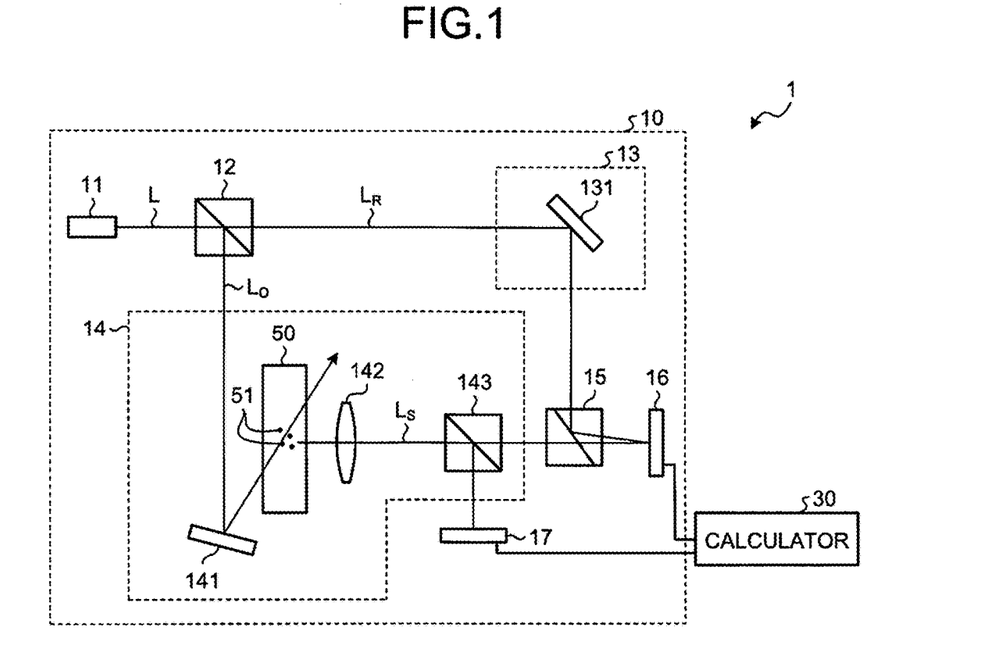
FIG. 1 is a diagram schematically illustrating a configuration example of a measuring apparatus according to an embodiment.
Figure 2:
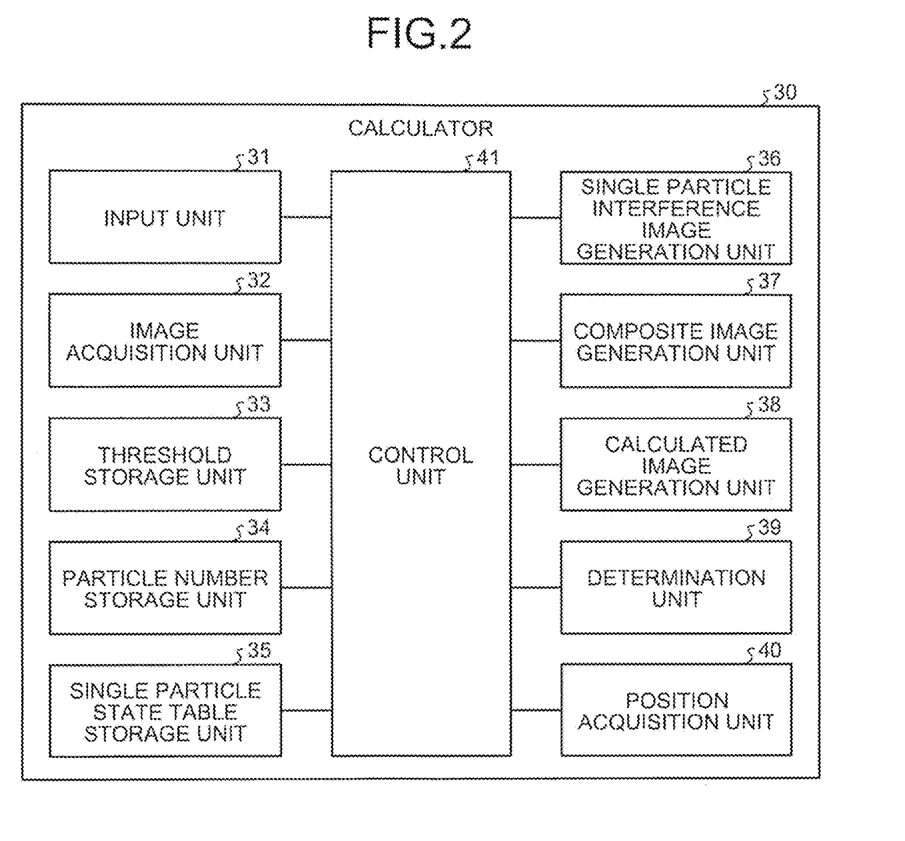
FIG. 2 is a block diagram schematically illustrating a functional configuration example of a calculator according to the embodiment.

FIG. 1 is a diagram schematically illustrating a configuration example of a measuring apparatus according to an embodiment. FIG. 2 is a block diagram schematically illustrating a functional configuration example of a calculator according to the embodiment. The measuring apparatus 1 includes an interference pattern generation part 10 and a calculator 30 serving as an arithmetic device. The interference pattern generation part 10 images a first interference pattern formed by scattered light $L_S$ and reference light $L_R$, and a second interference pattern formed by the scattered light $L_S$. The scattered light $L_S$ is obtained by irradiating a sample 50 containing inspection object particles 51 with object light $L_O$ that is given by splitting laser light from a laser light source 11. The reference light $L_R$ is given by splitting the laser light from the laser light source 11. The sample 50 is exemplified by a sample containing, for example, the particles 51.

The interference pattern generation part 10 includes the laser light source 11, a beam splitter 12, a reference light optical system 13, an object light optical system 14, a half mirror 15, an imaging device 16, and an imaging device 17. The laser light source 11 emits laser light L, which is coherent light. As the laser light source 11, for example, a semiconductor laser with a wavelength of 405 nm or the like may be used. The beam splitter 12 splits the laser light L emitted from the laser light source 11 into the object light $L_O$ to be made incident on the sample 50 and the reference light $L_R$ not to be made incident on the sample 50. Here, the beam splitter 12 reflects the object light $L_O$ and to transmit the reference light $L_R$.

The reference light optical system 13 includes an optical component for leading the reference light to the half mirror 15. Here, as the reference light optical system 13, a mirror 131 is provided that reflects the reference light $L_R$, which has been transmitted through the beam splitter 12, to the half mirror 15.

The object light optical system 14 includes optical components for irradiating the sample 50 with the object light $L_O$, and for leading light from the sample 50 to the half mirror 15. The object light optical system 14 includes a mirror 141, an objective lens 142, and a beam splitter 143. The mirror 141 changes the optical path of the object light $L_O$, which has been reflected by the beam splitter 12, to irradiate the sample 50 with the object light $L_O$. The objective lens 142 is a lens that converts the wave front of the scattered light $L_S$, which has been scattered by the particles 51 in the sample 50, to form respective interference patterns on the imaging devices 16 and 17. The beam splitter 143 splits the scattered light $L_S$, which has been transmitted through the objective lens 142, into a portion to an optical path leading to the imaging device 17 side and a portion to an optical path leading to the half mirror 15 side.

The half mirror 15 multiplexes the reference light $L_R$, which has passed through the reference light optical system 13, and the scattered light $L_S$, which has been scattered by the particles 51 in the sample 50 in the object light optical system 14, and leads the resultant light to the imaging device 16. Here, the half mirror 15 reflects the reference light $L_R$ to the imaging device 16, and transmits the scattered light $L_S$ to the imaging device 16.

The imaging device 16 images a first interference image, which is an interference pattern formed by the scattered light $L_S$ and the reference light $L_R$, and outputs the first interference image to the calculator 30. The imaging device 17 images a second interference image, which is an interference pattern formed by the scattered light $L_S$ from the plurality of particles 51, and outputs the second interference image to the calculator 30. As the imaging devices 16 and 17, for example, a Charge-Coupled Device (CCD) image sensor or Complementary Metal-Oxide-Semiconductor (CMOS) image sensor may be used. Here, the imaging device 16, the imaging device 17, and the half mirror 15 are arranged such that the optical distance between the beam splitter 143 and the imaging device 16 is equal to the optical distance between the beam splitter 143 and the imaging device 17.

The calculator 30 compares a composite image generated by combining the first interference image and the second interference image, with a calculated image obtained by combining single particle interference images. Each of the single particle interference images is an interference image that is expected to be obtained by the imaging device 16 in the case where a particle 5 is present alone in the sample 50. The composite image is an image obtained by removing the second interference image and the light intensity solely of the reference light $L_R$ from the first interference image. Each single particle interference image is an interference image obtained by the imaging device 16 if a single particle 5 is present alone in the sample 50. There are single particle interference images in number equal to the number of particle states of the single particle. Each particle state may be exemplified by a combination of the position of a particle 51 in the sample 50 with the complex amplitude of scattered light $L_S$. When the composite image agrees with the calculated image, the calculator 30 determines that particles are present at particle positions that have been used for calculation of the calculated image.

Here, an explanation will be given in detail of a method for estimating the position of each particle 51 in the sample 50 (liquid) by the calculator 30. When the particles 51 in the sample 50 are sufficiently small, the scattered light $L_S$ from the respective particles 51 can be thought as superposition of spherical waves radiated from the respective particles 51, each of which is considered as a point light source. Light intensity distribution $\varphi$ formed on the imaging device 17 by scattered light $L_S$ scattered by N-number of particles 51 is given by the following formula (1), where $E_n$ (n=1, 2, ..., or N) denotes the complex amplitude of an electric field formed by scattered light $L_S$ from each particle 51.

$$\varphi = \left(\sum_{n=1}^{N} E_n\right)\left(\sum_{n=1}^{N} E_n\right)^* \tag{1}$$

On the other hand, when the optical distance between the beam splitter 143 and the imaging device 16 is set equal to the optical distance between the beam splitter 143 and the imaging device 17, light intensity distribution $\psi$ formed on the imaging device 16 is given by the following formula (2), where $E_r$ denotes the complex amplitude of an electric field formed by the reference light $L_R$.

$$\psi = \left(E_r + \sum_{n=1}^{N} E_n\right)\left(E_r + \sum_{n=1}^{N} E_n\right)^* \tag{2}$$

An interference pattern given by the formula (2) contains interference between scattered light $L_S$ and scattered light $L_S$ from the respective particles 51, and thus is complicated. Accordingly, when consideration is given to "$\psi - \varphi$", the following formulas (3-1) and (3-2) can be obtained from the formulas (1) and (2). Here, $I_r$ is expressed by the following formula (4), and $I_n$ is expressed by the following formula (5).

$$\psi - \varphi = E_r E_r^* + \sum_{n=1}^{N}(E_r E_n^* + E_r^* E_n) \tag{3-1}$$

$$= I_r + \sum_{n=1}^{N} I_n \tag{3-2}$$

$$I_r = E_r E_r^* \tag{4}$$

$$I_n = E_r E_n^* + E_r^* E_n \tag{5}$$

Here, in the formula (3-2), $I_r$ denotes the light intensity solely of the reference light $L_R$, and $I_n$ denotes an interference pattern formed by scattered light $L_S$, which is generated in the case where each particle 51 is present alone, and the reference light $L_R$. The light intensity $I_r$ solely of the reference light $L_R$ can be a known parameter by performing measurement in advance while blocking off the object light $L_O$. In consideration of the above, the result of subtracting $I_r$ from the formula (3-2) is assumed to be composite light intensity distribution $\eta$, as expressed in the following formula (6).

$$\eta = \sum_{n=1}^{N}(E_r E_n^* + E_r^* E_n) = \sum_{n=1}^{N} I_n \tag{6}$$

Figure 3A:
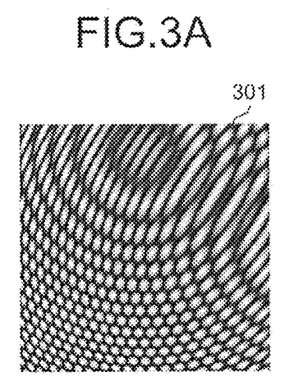
FIGS. 3A to 3C are diagrams schematically illustrating a method for obtaining composite light intensity distribution from actual interference patterns.
Figure 3B:
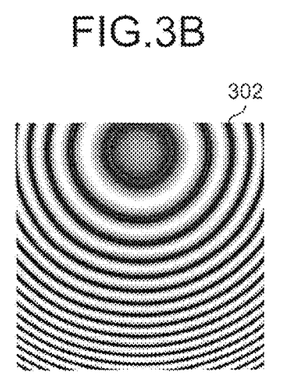
Figure 3C:
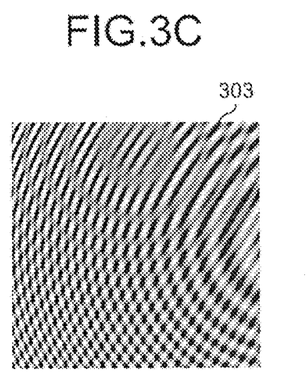

FIGS. 3A to 3C are diagrams schematically illustrating a method for obtaining the composite light intensity distribution from actual interference patterns. As illustrated in FIG. 3A, in actual measurement, a first interference image 301, which is represented by the light intensity distribution $\psi$ on the imaging device 16 in the formula (2), is obtained by the imaging device 16. Further, as illustrated in FIG. 3B, a second interference image 302, which is represented by the light intensity distribution $\varphi$ on the imaging device 17 in the formula (1), is obtained by the imaging device 17. The first interference image 301 and the second interference image 302 are transferred to the calculator 30, and a composite image 303, which is represented by the composite light intensity distribution $\eta$ in the formula (6), is obtained by the calculation described above. Specifically, the composite image 303 illustrated in FIG. 3C is calculated by the calculator 30 by subtracting the second interference image 302 of FIG. 3B and the light intensity $I_r$ solely of the reference light $L_R$, which is an offset component, from the first interference image 301 of FIG. 3A.

Figure 4:
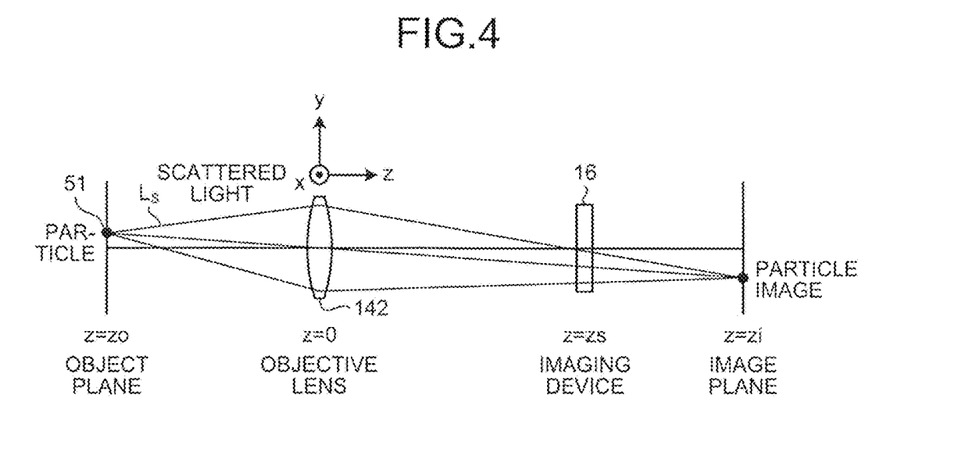
FIG. 4 is a diagram schematically illustrating a state where scattered light scattered by a single particle is being transmitted through an objective lens.

Incidentally, the complex amplitude $E_n$ (n=1, 2, ..., or N) of an electric field formed by scattered light $L_S$ from each particle 51 can be calculated on the basis of the position of each particle 51, the focal distance of the objective lens 142, and the position of the imaging device 16. FIG. 4 is a diagram schematically illustrating a state where scattered light scattered by a single particle is being transmitted through the objective lens. Here, a coordinate system is defined where the principal point of the objective lens 142 is the origin and the z-axis agrees with the optical axis. Where it is assumed that the position of the particle 51 is Po=(x, y, zo) and the position of an image of the particle 51 (image point) is Pi=(x', y', zi), the relations of the following formulas (7) to (9) hold on the basis of lens formulas. Here, "f" denotes the focal distance of the objective lens 142, and M is a lateral magnification M=zi/zo.

$$x' = Mx \qquad (7)$$

$$y' = My \qquad (8)$$

$$zi = \frac{zo + f}{zo \cdot f} \qquad (9)$$

Since the scattered light $L_S$ in an image space is a spherical wave about the image point Pi as the center, the complex amplitude $E_n$ at a point Ps=(x", y", zs) on the imaging device 16 arranged at z=zs is expressed by the following formula (10). Here, "k" denotes a wave number, and A is a complex number indicating the size of amplitude.

$$E_n = A \exp[ik\sqrt{(x''-x')^2+(y''-y')^2+(zs-zi')^2}] \qquad (10)$$

Further, where the reference light $L_R$ is assumed to have uniform light intensity distribution for the sake of simplicity, the complex amplitude $E_r$ of the reference light $L_R$ at the point Ps=(x", y", zs) on the imaging device 16 is expressed by the following formula (11). Here, $A_r$ is a complex number indicating amplitude, and $k_{rx}$, $k_{ry}$, and $k_{rz}$ are the x, y, and z components of the wave vector of the reference light $L_R$ and satisfy the following formula (12).

$$E_r = A_r \exp[i(k_{rx}x''+k_{ry}y''+k_{rz}zs)] \qquad (11)$$

$$k_{rx}^2 + k_{ry}^2 + k_{rz}^2 = k^2 \qquad (12)$$

When the formulas (7) to (11) are used to calculate the composite light intensity distribution q of the formula (6), it should be possible to obtain a composite image the same as that to be obtained from actual measurement results. However, in order to achieve this, it is necessary to know the number N of particles (particle number N) in the sample 50, and the position of each particle 51 and the complex amplitude of scattered light $L_S$ ($x_i$, $y_i$, $zo_i$, $A_i$) (i=1, 2, ..., or N). On the other hand, it may be assumed conversely that the position ($x_i$, $y_i$, $zo_i$) of each particle 51 and the complex amplitude $A_i$ of scattered light $L_S$ are suitably decided, to calculate the composite light intensity distribution η by using the formula (6). In this case, when the calculation result of the composite light intensity distribution η agrees with the composite image, it can be estimated that each particle 51 is present at the position suitably decided.

Accordingly, first, a particle position Po in the sample 50, which is an unknown quantity, and the complex amplitude A of scattered light $L_S$ are used to create a single particle state table serving as single particle state information. The single particle state table is formed such that the particle position Po and the complex amplitude A of scattered light $L_S$ are discretely assumed, and combinations of a particle position Po and a complex amplitude A of scattered light $L_S$, thus assumed, are compiled. The single particle state table contains $T_{size}$-number of elements (particle states) ($x_i$, $y_i$, $zo_i$, $A_i$), which are combinations of a particle position Po and a complex amplitude A of scattered light $L_S$. Then, for each of the elements, the formulas (7) to (11) are used to obtain the complex amplitude $E_n$ at the point Ps on the imaging device 16 and the complex amplitude $E_r$ of the reference light $L_R$ at the point Ps on the imaging device 16. Further, the formula (5) is used to calculate an interference pattern $I_n$ formed by scattered light $L_S$, which is to be generated in the case where each particle 51 is present alone, and the reference light $L_R$, and thereby obtain a single particle interference image. Each single particle interference image is correlated with a particle state used as the basis for calculation, and is stored in the single particle state table.

Thereafter, a value of the particle number N is suitably decided, and single particle interference images corresponding to N-number of elements selected from the single particle state table are used to composite a calculated image by applying the formula (6).

Figure 5A:
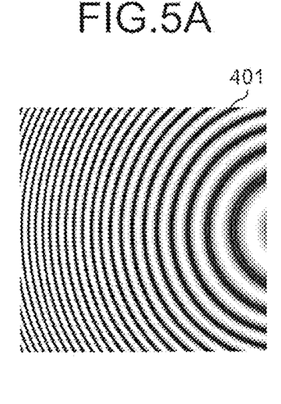
FIGS. 5A to 5C are diagrams schematically illustrating a method for obtaining a calculated image from single particle interference images by calculation.
Figure 5B:
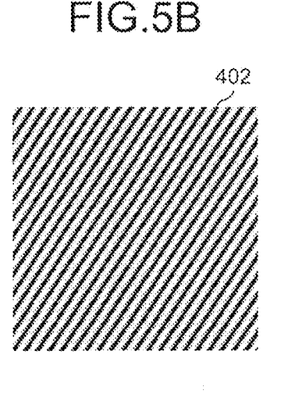
Figure 5C:
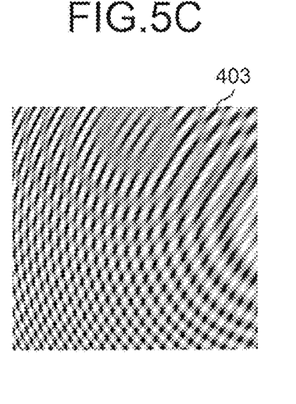

FIGS. 5A to 5C are diagrams schematically illustrating a method for obtaining the calculated image from single particle interference images by calculation. For example, FIG. 5A illustrates a single particle interference image 401 corresponding to an element ($x_1$, $y_1$, $zo_1$, $A_1$). FIG. 5B illustrates a single particle interference image 402 corresponding to an element ($x_2$, $y_2$, $zo_2$, $A_2$). Then, these two single particle interference images 401 and 402 are combined in accordance with the formula (6), and a calculated image 403 illustrated in FIG. 5C is thereby obtained.

In order to compare the composite image with the calculated image, for example, the residual sum of square (Residual Sum of Square: RSS) of pixel values is used. A threshold $RSS_{th}$ is set in advance for the residual sum of square RSS of pixel values, and the calculated image is compared with the composite image, while the combination and/or the particle number N are varied for selecting N-number of elements from the single particle state table, until a residual sum of square RSS of pixel values smaller than the threshold $RSS_{th}$ is obtained. Specifically, when the residual sum of square RSS of pixel values is larger than the threshold $RSS_{th}$, it is determined that the composite image does not agree with the calculated image. When the residual sum of square RSS of pixel values is smaller than the threshold $RSS_{th}$, it is determined that the composite image agrees with the calculated image. Here, when the residual sum of square RSS of pixel values is equal to the threshold $RSS_{th}$, it may be determined that the composite image agrees with the calculated image, or it may be determined that the composite image does not agree with the calculated image.

When the calculated image agrees with the composite image, ($x_k$, $y_k$, $zo_k$) (k is an integer from 1 to N) in the selected N-number of elements is the position of each particle 51 that has been sought. For example, in comparison of the composite image 303 of FIG. 3C with the calculated image 403 of FIG. 5C, they agree with each other. Thus, the positions in the elements correlated with the single particle interference images 401 and 402, which have been used to obtain the calculated image 403 of FIG. 5C, are the positions of particles 51 present in the sample 50.

In order to estimate the position of each particle 51 by using the above method, as illustrated in FIG. 2, the calculator 30 according to this embodiment includes an input unit 31, an image acquisition unit 32, a threshold storage unit 33, a particle number storage unit 34, a single particle state table storage unit 35, a single particle interference image generation unit 36, a composite image generation unit 37, a calculated image generation unit 38, a determination unit 39, a position acquisition unit 40, and a control unit 41 that controls these processing parts.

The input unit 31 is an interface for users to input information necessary for position estimation. The input unit 31 is composed of a keyboard and so forth. From the input unit 31, information is input, such as a threshold $RSS_{th}$, a minimum value $N_{min}$ and a maximum value $N_{max}$ of the particle number N that have been assumed, a particle position $Po_i$ and a complex amplitude $A_i$ of scattered light that have been assumed. The image acquisition unit 32 acquires the first interference image from the imaging device 16, and acquires the second interference image from the imaging device 17.

The threshold storage unit 33 stores the threshold $RSS_{th}$ input from the input unit 31. The particle number storage unit 34 stores the minimum value $N_{min}$ and the maximum value $N_{max}$ of the particle number N that have been assumed and input from the input unit 31.

Figure 6:
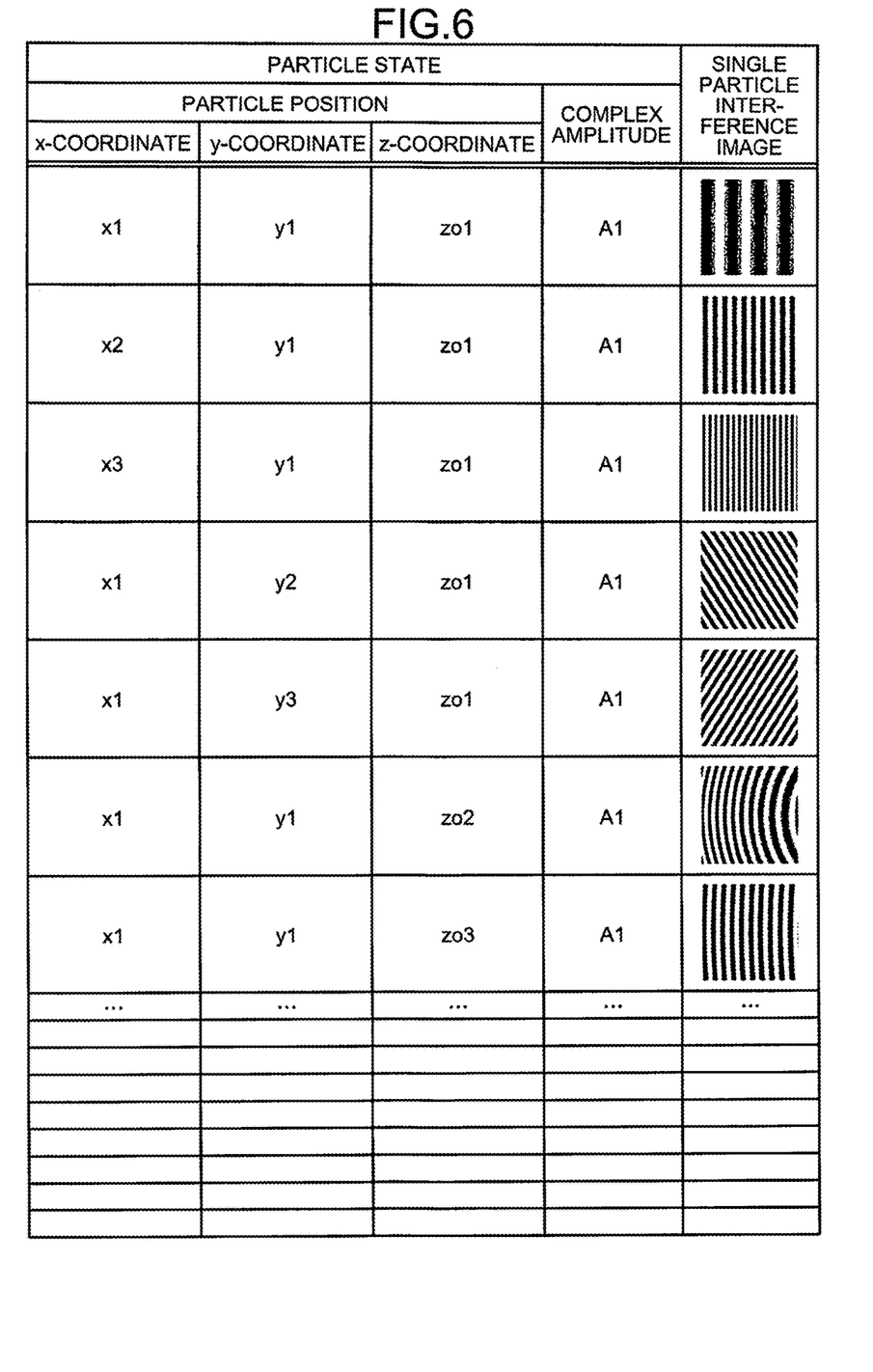
FIG. 6 is a diagram illustrating an example of a single particle state table.

The single particle state table storage unit 35 stores the single particle state table. As described above, the single particle state table provides information about particle states and single particle interference images in correlation with each other. FIG. 6 is a diagram illustrating an example of the single particle state table. As illustrated in FIG. 6, the single particle state table includes sets of a particle position $Po_i$ ($x_i$, $y_i$, $zo_i$) in the sample 50, a complex amplitude $A_i$ of scattered light $L_S$, and a single particle interference image. A particle position in the sample 50 is combined with a complex amplitude $A_i$ of scattered light $L_S$ to define each particle state. Where a combination of a particle position $Po_i$, a complex amplitude $A_i$ of scattered light $L_S$, and a single particle interference image is referred to as an element of the single particle state table, the single particle state table contains $T_{size}$-number of elements. Here, in this example, each particle state is a combination of a particle position with a complex amplitude $A_i$ of scattered light $L_S$; however, it suffices that each particle state includes at least particle position.

A combination of the position $Po_i$ of a single particle and the complex amplitude $A_i$ of scattered light $L_S$ from the single particle at this position $Po_i$, which serves as the basis of a single particle interference image, is input from the input unit 31, and is stored as a particle state ($x_i$, $y_i$, $zo_i$, $A_i$) in the single particle state table. Particle states are set such that single particle positions are discrete. Here, when the number of inputs to be made is large, it may be adopted to input respective ranges of the particle position $Po_i$ and the complex amplitude $A_i$, which can be taken, and to select values from these ranges arbitrarily or in accordance a certain rule, thereby define particle states.

Figure 7A:
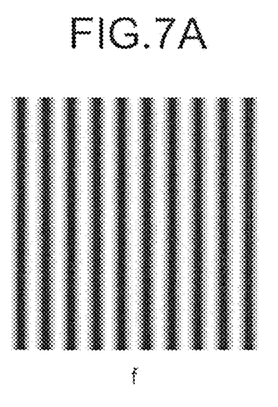
FIGS. 7A to 7C are diagrams illustrating examples of a single particle interference image different from each other because of difference in position in an x-direction.
Figure 7B:
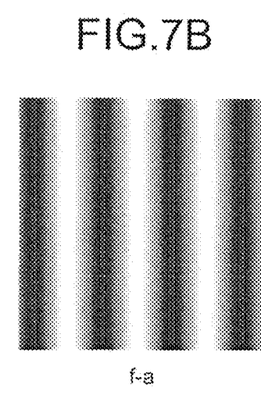
Figure 7C:
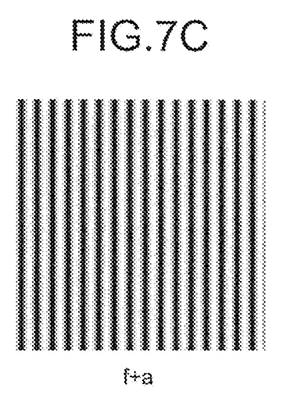
Figure 8A:
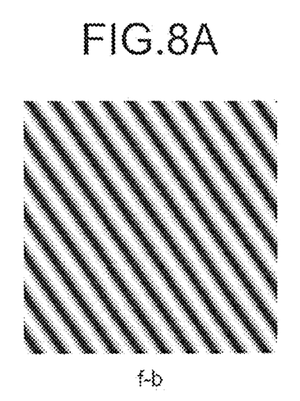
FIGS. 8A and 8B are diagrams illustrating examples of a single particle interference image different from each other because of difference in position in a y-direction.
Figure 8B:
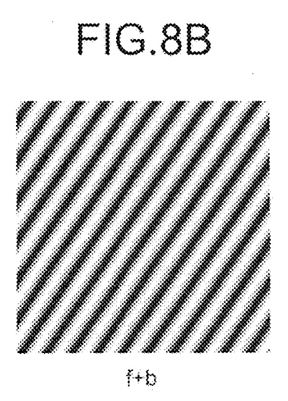
Figure 9A:
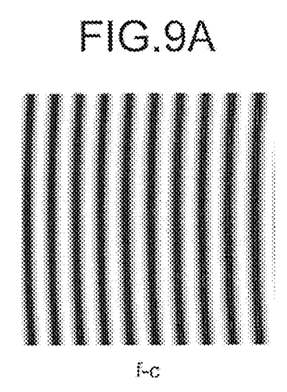
FIGS. 9A and 9B are diagrams illustrating examples of a single particle interference image different from each other because of difference in position in a z-direction.
Figure 9B:
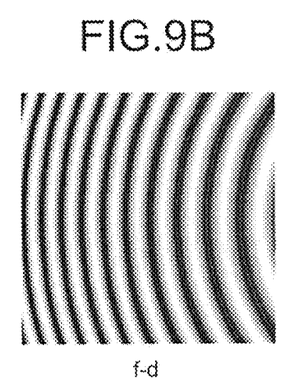

FIGS. 7A to 7C are diagrams illustrating examples of a single particle interference image different from each other because of difference in position in an x-direction. FIGS. 8A and 8B are diagrams illustrating examples of a single particle interference image different from each other because of difference in position in a y-direction. FIGS. 9A and 9B are diagrams illustrating examples of a single particle interference image different from each other because of difference in position in a z-direction.

FIG. 7A illustrates a single particle interference image when a single particle is present at the focal point "f". In this case, linear interference fringes at certain intervals are generated by the single particle. When the single particle position is shifted by "−a" (a>0) in the x-direction from the state of FIG. 7A, the intervals of interference fringes become larger as illustrated in FIG. 7B. On the other hand, when the single particle position is shifted by "+a" in the x-direction from the state of FIG. 7A, the intervals of interference fringes become smaller as illustrated in FIG. 7C. Thus, when the single particle is moved from the focal point "f" in the x-direction, the intervals of interference fringes are changed.

When the single particle position is shifted by "−b" (b>0) in the y-direction from the state of FIG. 7A, interference fringes are rotated counterclockwise as illustrated in FIG. 8A. On the other hand, when the single particle position is shifted by "+b" in the y-direction from the state of FIG. 7A, interference fringes are rotated clockwise as illustrated in FIG. 8B. Thus, when the single particle is moved from the focal point "f" in the y-direction, interference fringes are rotated.

When the single particle position is shifted by "−c" or "−d" (d>c>0) in the z-direction from the state of FIG. 7A, curved interference fringes are generated as illustrated in FIG. 9A or 9B. Further, as the shift amount in the z-direction is increased, the curve of interference fringes tends to become larger. Thus, when the single particle is moved from the focal point "f" in the z-direction, interference fringes are curved.

Here, FIGS. 9A and 9B illustrate cases where the particle position is shifted in the z-axis negative direction; however, the same changes are caused where the particle position is shifted in the positive direction. In the case where the sample 50 is arranged over a range from a positive region to a negative region in the z-direction to include the focal plane, it becomes impossible to distinguish whether the obtained single particle interference image is due to a positional change of the single particle in the z-axis positive direction or due to a positional change in the negative direction. In consideration of this, when position measuring is to be actually preformed, the sample 50 is arranged not to be present over the focal plane, and it is determined whether the position of the sample 50 is located on the forward side in the object light traveling direction (the objective lens side, or z-axis positive side) from the focal plane, or the position is located on the backward side in the object light traveling direction (the side opposite to the objective lens, or z-axis negative side) from the focal plane.

With reference to the focal point, when the sample 50 is arranged on the forward side in the object light traveling direction, each particle 51 is positioned on the z-axis positive direction side from the focal plane, and thus is never positioned on the negative direction side. Accordingly, the sign for expressing a shift position becomes reverse to that of the cases of FIGS. 9A and 9B. Specifically, when the single particle is present at a position shifted by "c" in the z-axis positive direction from the focal point, the interference fringes of FIG. 9A are observed. When the single particle is present at a position shifted by "d" in the z-axis positive direction, the interference fringes of FIG. 9B are observed. On the other hand, with reference to the focal plane, when the sample 50 is arranged on the backward side in the object light traveling direction, each particle 51 is positioned on the z-axis negative direction side from the focal plane, and thus is never positioned on the positive direction side. In this case, the interference fringes illustrated in FIGS. 9A and 9B are used.

As described above, when the single particle position is merely shifted in the x-axis direction, y-axis direction, or z-axis direction from the focal point, interference fringes are changed in various ways. Accordingly, the single particle state table is made to store sets of interference fringes for various particle positions $Po_i$ ($x_i$, $y_i$, $zo_i$), so that various combinations of interference fringes can be achieved. Further, even at a certain particle position $Po_i$, interference fringes can be changed by a difference of the complex amplitude $A_i$ of scattered light $L_S$. Accordingly, the single particle state table is made to store various combinations of a particle position $Po_i$ and a complex amplitude $A_i$ of scattered light $L_S$, as particle states.

The single particle interference image generation unit 36 generates a single particle interference image by using the formulas (7) to (11), for each particle state input in the single particle state table. The single particle interference image is an interference pattern to be formed on the imaging device 16 by scattered light $L_S$, which has been generated by a single particle having a selected particle state, and the reference light $L_R$. Further, as illustrated in FIG. 6, the single particle interference image generation unit 36 stores the single particle interference image thus generated into the single particle state table, in a state correlated with the particle state used as the basis for generating this single particle interference image.

The composite image generation unit 37 generates a composite image by using the first interference image and the second interference image acquired by the image acquisition unit 32 and the light intensity solely of the reference light $L_R$. As described above, the composite image generation unit 37 generates a composite image by subtracting the second interference image and the light intensity solely of the reference light $L_R$ from the first interference image. Here, the light intensity solely of the reference light $L_R$ can be calculated as an offset component that serves as a constant.

The calculated image generation unit 38 generates a calculated image from the single particle state table. Specifically, the calculated image generation unit 38 assumes that N-number of particles are present in the liquid, and generates a calculated image by acquiring single particle interference images corresponding to N-number of particle states from the single particle state table. This generation of a calculated image is performed to each of combinations variously selected from the elements in the single particle state table, for the N-number of particles. Further, in the determination unit 39 described below, when no agreement with the composite image is reached by any of the combinations for this value of the particle number N, the generation of a calculated image is performed in the same way for another value of the particle number N between the minimum value $N_{min}$ and the maximum value $N_{max}$ of the particle number N.

The determination unit 39 compares the composite image composited by the composite image generation unit 37 with the calculated image generated by the calculated image generation unit 38, and determines whether the two images agree with each other. In order to compare the images with each other, for example, the residual sum of square of pixel values described above is used. When determining that the two images agree with each other, the determination unit 39 gives notice of information indicating this agreement to the calculated image generation unit 38 and the position acquisition unit 40. Consequently, the calculated image generation unit 38 stops the processing for generating a calculated image. On the other hand, when determining that the two images do not agree with each other, the determination unit 39 gives notice of information indicating this disagreement to the calculated image generation unit 38. Consequently, the calculated image generation unit 38 continues the processing for generating a calculated image.

When receiving information indicating agreement between the composite image and a calculated image from the determination unit 39, the position acquisition unit 40 acquires the particle positions of N-number of particles, which have been used for the calculated image with the agreement, from the single particle state table, and outputs these positions as the positions of particles 51 in the sample 50. This is because the particle positions of N-number of particles used for the calculated image with the agreement are estimated to be the positions of particles 51 in the sample 50 measured by the interference pattern generation part 10. For example, the position acquisition unit 40 outputs the positions of particles 51 to a display unit (not illustrated). When receiving information indicating disagreement between the composite image and a calculated image from the determination unit 39 for each of all the combinations within the ranges of all values of the particle number N, the position acquisition unit 40 outputs information indicating that no solution is included in the assumed sets of a value of the particle number N and elements (particle states), to the display unit (not illustrated), for example.

Here, the threshold storage unit 33, the particle number storage unit 34, and the single particle state table storage unit 35 may be formed of a volatile memory or may be formed of a nonvolatile memory.

Figure 10:
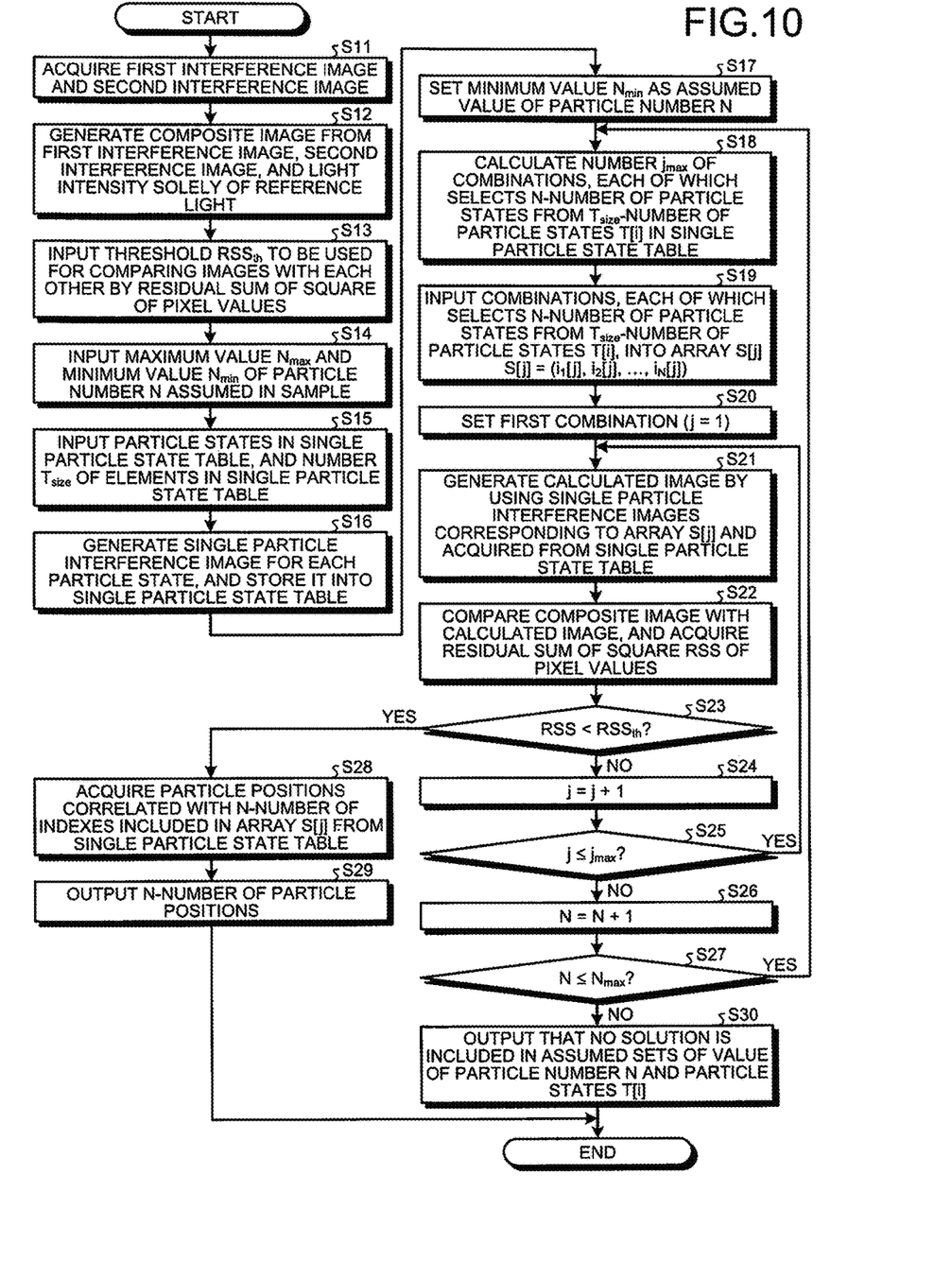
FIG. 10 is a flowchart illustrating an example of the sequence of a measuring method according to the embodiment.

Next, an explanation will be given of a measuring method in the measuring apparatus 1 having the configuration described above. FIG. 10 is a flowchart illustrating an example of the sequence of a measuring method according to the embodiment. First, the laser light source 11 emits laser light L to irradiate the sample 50 with the laser light L. The imaging device 16 picks up a first interference pattern formed by interference between scattered light $L_S$ from particles 51 in a sample 50 and reference light $L_R$. The imaging device 17 picks up a second interference pattern formed by scattered light $L_S$ from the particles 51 in the sample 50. The imaging device 16 images the first interference pattern, and thereby obtains a first interference image. The imaging device 17 images the second interference pattern, and thereby obtains a second interference image. The image acquisition unit 32 of the calculator 30 acquires the first interference image from the imaging device 16, and acquires the second interference image from the imaging device 17 (step S11). Then, the composite image generation unit 37 subtracts the second interference image and the light intensity solely of the reference light $L_R$ from the first interference image, and thereby generates a composite image (step S12).

Thereafter, a threshold $RSS_{th}$ to be used for comparing images with each other by the residual sum of square of pixel values is input from the input unit 31 by a user (step S13), and is stored into the threshold storage unit 33. Further, a maximum value $N_{max}$ and a minimum value $N_{min}$ of the particle number N assumed in the sample 50 are input from the input unit 31 by the user (step S14), and are stored into the particle number storage unit 34.

Thereafter, particle states in the single particle state table and the number $T_{size}$ of elements (particle states) in the single particle state table are input (step S15). For example, combinations of a particle position ($x_i$, $y_i$, $zo_i$) and a complex amplitude A of scattered light $L_S$ from a single particle present at the particle position are generated such that single particle positions are discrete, and the combinations thus generated are input as particle states into the single particle state table. The particle states may be input by a user of the measuring apparatus 1, or may be generated by the calculator 30. Each of the particle states in the single particle state table will be denoted by T[i] (i=1 to $T_{size}$).

Then, the single particle interference image generation unit 36 generates a single particle interference image by applying the formulas (7) to (11) to each particle state T[i] in the single particle state table. The single particle interference image generation unit 36 stores the single particle interference image thus generated into the single particle state table, in a state correlated with the particle state T[i] used as the basis for calculation (step S16).

Thereafter, the calculated image generation unit 38 sets the minimum value $N_{min}$ given in step S14, as an assumed value of the particle number N (step S17). Further, the calculated image generation unit 38 calculates the number $j_{max}$ of combinations (combination number $j_{max}$), each of which selects N-number of particle states from the $T_{size}$-number of particle states T[i] in the single particle state table (step S18). The combination number $j_{max}$ is calculated by the following formula (13).

$$j_{max} = {}_{T_{size}}C_N \qquad (13)$$

Then, combinations, each of which selects N-number of particle states T[i] from the $T_{size}$-number of particle states T[i] in the single particle state table, are input into an array S[j] (step S19). Here, where an index indicating each element (particle state) in the single particle state table is denoted by $i_k[j]$ (k=1 to N), the array S[j] is expressed by the following formula (14). Further, "j" is an index attached to each combination of selecting N-number of particle states from the $T_{size}$-number of particle states T[i], and its maximum value is $j_{max}$.

$$S[j] = (i_1[j], i_2[j], \ldots, i_N[j]) \qquad (14)$$

Thereafter, the calculated image generation unit 38 sets the first combination (j=1) from the $j_{max}$-number of combinations (step S20), acquires the single particle interference images corresponding to the array S[j], and generates a calculated image by using the formula (6) (step S21). Specifically, the calculated image generation unit 38 acquires indexes ($i_1[1], i_2[1], \ldots, i_N[1]$ in this case) included in the array S[j] (an array S[1] in this case), and acquires the single particle interference images correlated with the respective indexes from the single particle state table. The formula (6) expresses that a calculated image is obtained by adding up N-number of single particle interference images. Here, each single particle interference image is an interference pattern $I_n$ formed by the reference light $L_R$ and scattered light $L_S$, which is generated in the case where a single particle is present alone.

Then, the determination unit 39 compares the composite image generated in step S12 with the calculated image generated in step S21, and determines whether these two images agree with each other. Specifically, the determination unit 39 compares the composite image with the calculated image, and acquires a residual sum of square RSS of pixel values (step S22). Then, the determination unit 39 determines whether the residual sum of square RSS of pixel values is smaller than the threshold $RSS_{th}$ set in step S13 (step S23).

When the residual sum of square RSS of pixel values is larger than the threshold $RSS_{th}$ (No at step S23), it is indicated that the calculated image is different from the composite image. Accordingly, the determination unit 39 adds one to the current value of "j" to set a new value of "j" (step S24), and determines whether the new value of "j" is equal to or less than max (step S25). The processing performed here means that, as the calculated image is different from the composite image in the case of the "j"-th combination (here, j=1) used for the current calculation, new calculation is to be performed by using the "j+1"-th combination. Further, it is also confirmed whether the "j+1"-th combination is equal to or less than $j_{max}$. When the new value of "j" is equal to or less than $j_{max}$ (Yes at step S25), the processing from step S21 is subsequently executed again.

On the other hand, when the new value of "j" is larger than $j_{max}$ (No at step S25), this means that calculation has been performed by using all the combinations for the current value of the particle number N, and means that the obtained composite image does not come from particles in the currently set value of the particle number N. Accordingly, the calculated image generation unit 38 adds one to the current value of the particle number N to set a new value of the particle number N (step S26), and determines whether the new value of the particle number N is equal to or less than N. (step S27). When the new value of N is equal to or less than $N_{max}$ (Yes at step S27), the processing from step S18 is subsequently executed.

In step S23, when the residual sum of square RSS of pixel values is smaller than the threshold $RSS_{th}$ (Yes at step S23), it is indicated that the calculated image agrees with the composite image. Accordingly, the determination unit 39 gives the array S[j], which has been used for generation of the calculated image in step S21, to the position acquisition unit 40. The position acquisition unit 40 acquires the particle positions correlated with the N-number of indexes included in the array S[j] thus given, from the single particle state table (step S28). Then, the position acquisition unit 40 outputs the N-number of particle positions thus acquired to the display unit or the like, for example, (step S29). As a result, the processing sequence ends.

Further, in step S27, when the new value of N is larger than $N_{max}$ (No at step S27), it is output that no solution (about the number of particles and particle states) to agree with the composite image is included in the sets of an assumed value of the particle number N and assumed particle states T[i] (step S30). As a result, the processing sequence ends.

Here, flows of the processing to obtain a calculated image and compare this calculated image with the composite image are independent of each other, and thus may be performed in parallel with each other. In this case, the processing rate is increased. For example, in the case of the processing to generate a calculated image for the "j"-th combination of a value of the particle number N set in step S17 and compare this calculated image with the composite image, a plurality of flows of the processing can be executed in parallel with each other.

The measuring apparatus and the measuring method described above may be applied to measurement of the positions of foreign substances in liquid, measurement of foreign substances in gas, or measurement of foreign substances in solid. For example, the measuring apparatus and the measuring method described above may be used for measuring the positions of foreign substances in a resist inside a container that stores the resist to be used for imprint processing.

Figure 11:
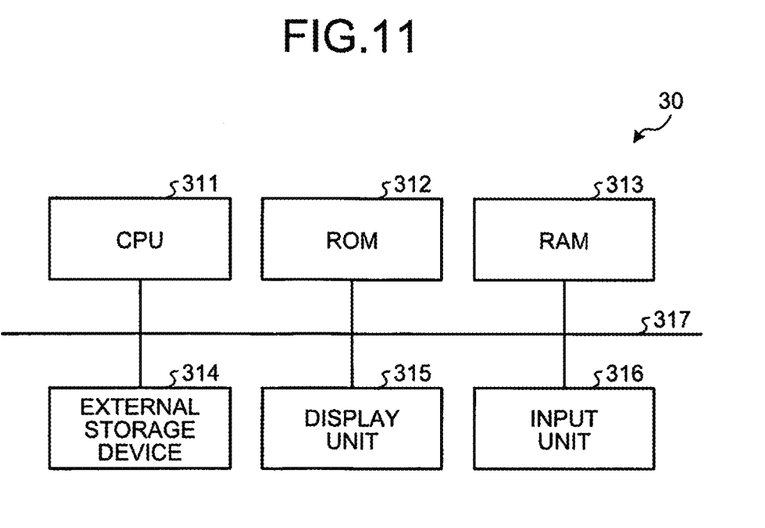
FIG. 11 is a block diagram illustrating a hardware configuration example of the calculator.

Next, an explanation will be given of the hardware configuration of the calculator 30 of the measuring apparatus according to this embodiment. FIG. 11 is a block diagram illustrating a hardware configuration example of the calculator. The calculator 30 according to this embodiment has a hardware configuration utilizing an ordinary computer, in which a Central Processing Unit (CPU) 311, a Read Only Memory (ROM) 312, a Random Access Memory (RAM)

313 serving as the main storage device, an external storage device 314, such as a Hard Disk Drive (HDD) or Compact Disc (CD) drive device, a display unit 315, such as a display device, and an input unit 316, such as a keyboard and/or a mouse, are included, and are connected to each other via a bus line 317.

A program to be executed by the calculator 30 of the measuring apparatus 1 according to this embodiment has been prepared to perform the method illustrated in FIG. 10. This program is provided in a state recorded in a computer-readable recording medium, such as a CD-ROM, flexible disk (FD), CD-R, or Digital Versatile Disk (DVD), by a file in an installable format or executable format.

Alternatively, a program to be executed by the measuring apparatus 1 according to this embodiment may be provided such that the program is stored in a computer connected to a network, such as the internet, and is downloaded via the network. Further, a program to be executed by the measuring apparatus 1 according to this embodiment may be provided such that the program is provided or distributed via a network, such as the internet.

Alternatively, a program according to this embodiment may be provided in a state incorporated in an ROM or the like in advance.

A program to be executed by the measuring apparatus 1 according to this embodiment is formed in a module configuration that contains the respective parts described above (the image acquisition unit 32, single particle interference image generation unit 36, composite image generation unit 37, calculated image generation unit 38, determination unit 39, and position acquisition unit 40). For actual hardware, the CPU (processor) reads the program from a storage medium, such as one described above, and executes the program to load the respective parts described above into the main storage device. Consequently, the image acquisition unit 32, single particle interference image generation unit 36, composite image generation unit 37, calculated image generation unit 38, determination unit 39, and position acquisition unit 40 are generated in the main storage device.

In this embodiment, a first interference pattern is imaged that has been formed by interference between scattered light $L_S$ scattered by particles 51 in the sample 50, and the reference light $L_R$. Further, a second interference pattern is imaged that has been formed by interference of the scattered light $L_S$ scattered by the particles 51 in the sample 50. Then, a composite image is obtained from the first interference image and the second interference image. Further, a calculated image is obtained by combining single particle interference images acquired from a single particle state table that stores single particle interference images for respective assumed particle states. Each single particle interference image is formed by interference between scattered light $L_S$, which is to be generated on the assumption that a single particle is present with a certain particle state in the sample 50, and the reference light $L_R$. Then, the composite image is compared with the calculated image. When these two images agree with each other, it is determined that the particle positions correlated with the single particle interference images used for calculation of the calculated image are the positions of the particles 51 in the sample 50. Consequently, an effect is obtained that can specify particle positions by simpler calculation as compared with complicated calculation necessary for reproduction of a hologram by DHPIV.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A measuring apparatus comprising:
a light source;
a beam splitter that splits light from the light source into first light and second light, the second light being used to irradiate a sample containing particles treated as measuring objects;
a first imaging device that images a first interference pattern formed by multiplexing third light, which has been generated by irradiating the particles with the second light, and the first light;
a second imaging device that images a second interference pattern formed by the third light; and
an arithmetic device that compares a composite image with a calculated image, the composite image being created by using a first interference image picked up by the first imaging device and a second interference image picked up by the second imaging device, the calculated image being obtained by combining single particle interference images, each of which is expected to be obtained by the first imaging device in a case where a particle is present alone in the sample.

2. The measuring apparatus according to claim 1, wherein the arithmetic device sets, as the composite image, an image obtained by subtracting light intensity distribution of the second interference pattern recorded in the second interference image from light intensity distribution of the first interference pattern recorded in the first interference image.

3. The measuring apparatus according to claim 2, wherein the arithmetic device sets, as the composite image, an image obtained by further subtracting light intensity solely of the first light from the light intensity distribution of the first interference pattern.

4. The measuring apparatus according to claim 1, wherein the arithmetic device obtains combinations of selecting k-number (k is a natural number) of single particle interference images from single particle state information in which particle states including particle positions are correlated with single particle interference images, generates the calculated image for each of the combinations, and compares the calculated image thus generated with the composite image.

5. The measuring apparatus according to claim 4, wherein, when no calculated image that agrees with the composite image is present in the combinations of selecting k-number of single particle interference images from the single particle state information, the arithmetic device changes particle number "k" within a predetermined range.

6. The measuring apparatus according to claim 1, wherein, when the composite image does not agree with the calculated image, the arithmetic device selects another combination of single particle interference images from single particle state information in which particle states including particle positions are correlated with single particle interference images, and composites the calculated image by using this other combination of single particle interference images thus selected.

7. The measuring apparatus according to claim 1, wherein, when the composite image agrees with the calculated image, the arithmetic device estimates particle positions correlated with selected single particle interference images to be positions of the particles.

8. The measuring apparatus according to claim 1, wherein the arithmetic device, by use of a residual sum of square of pixel values, which is of the composite image and the calculated image, determines that the composite image agrees with the calculated image when the residual sum of square is smaller than a predetermined value.

9. The measuring apparatus according to claim 4, wherein each particle state further includes a complex amplitude.

10. The measuring apparatus according to claim 1, further comprising an objective lens to transmit the third light, the third light being generated from the second light scattered by the particles.

11. The measuring apparatus according to claim 10, wherein the sample is arranged on an objective lens side from a focal plane of the objective lens, or arranged on a side opposite to an arrangement position of the objective lens with reference to the focal plane.

12. The measuring apparatus according to claim 1, wherein the sample is solid, liquid, or gas.

13. A measuring method comprising:
splitting light from a light source into first light and second light, the second light being used to irradiate a sample containing particles treated as measuring objects;
multiplexing third light, which has been scattered by the particles in the sample, and the first light;
imaging, by a first imaging device, a first interference pattern formed by multiplexing the first light and the third light;
imaging, by a second imaging device, a second interference pattern formed by the third light;
generating a composite image by using a first interference image obtained by imaging the first interference pattern, and a second interference image obtained by imaging the second interference pattern;
generating a calculated image by combining single particle interference images, each of which is expected to be obtained by the first imaging device in a case where a particle is present alone in the sample; and
comparing the composite image with the calculated image.

14. The measuring method according to claim 13, wherein, in the generating of the composite image, an image obtained by subtracting light intensity distribution of the second interference pattern recorded in the second interference image from light intensity distribution of the first interference pattern recorded in the first interference image is set as the composite image.

15. The measuring method according to claim 14, wherein, in the generating of the composite image, an image obtained by further subtracting light intensity solely of the first light from the light intensity distribution of the first interference pattern is set as the composite image.

16. The measuring method according to claim 13, wherein the generating of the calculated image includes
obtaining combinations of selecting k-number (k is a natural number) of single particle interference images from single particle state information in which particle states including particle positions are correlated with single particle interference images,
generating the calculated image for each of the combinations thus obtained, and
comparing the calculated image thus generated with the composite image.

17. The measuring method according to claim 16, wherein, in the generating of the calculated image, when no calculated image that agrees with the composite image is present in the combinations of selecting k-number of single particle interference images from the single particle state information, particle number "k" is changed within a predetermined range.

18. The measuring method according to claim 13, wherein, when the composite image does not agree with the calculated image in the comparing the composite image with the calculated image, the generating of the calculated image includes
selecting another combination of single particle interference images from single particle state information in which particle states including particle positions are correlated with single particle interference images, and compositing the calculated image by using this other combination of single particle interference images thus selected.

19. The measuring method according to claim 13, wherein the comparing of the composite image with the calculated image includes, by use of a residual sum of square of pixel values, which is of the composite image and the calculated image, determining that the composite image agrees with the calculated image when the residual sum of square is smaller than a predetermined value.

20. The measuring method according to claim 16, wherein each particle state further includes a complex amplitude.

* * * * *